(12) United States Patent
Taniguchi

(10) Patent No.: US 10,413,903 B2
(45) Date of Patent: Sep. 17, 2019

(54) DEVICES, SYSTEMS AND METHODS FOR LINEARIZATION OF POLYMERS

(71) Applicant: Osaka University, Osaka (JP)

(72) Inventor: Masateru Taniguchi, Osaka (JP)

(73) Assignee: Osaka University (JP)

( * ) Notice: Subject to any disclaimer, the term of this patent is extended or adjusted under 35 U.S.C. 154(b) by 108 days.

(21) Appl. No.: 15/340,584

(22) Filed: Nov. 1, 2016

(65) Prior Publication Data

US 2017/0144158 A1 May 25, 2017

Related U.S. Application Data

(63) Continuation of application No. PCT/JP2015/063963, filed on May 8, 2015.

(60) Provisional application No. 61/990,589, filed on May 8, 2014.

(51) Int. Cl.
| | | |
|---|---|---|
| *C12Q 1/6869* | (2018.01) | |
| *B01L 3/00* | (2006.01) | |
| *C12Q 1/6806* | (2018.01) | |
| *B82Y 10/00* | (2011.01) | |
| *B82Y 30/00* | (2011.01) | |

(52) U.S. Cl.
CPC ......... *B01L 3/502761* (2013.01); *B82Y 10/00* (2013.01); *B82Y 30/00* (2013.01); *C12Q 1/6806* (2013.01); *C12Q 1/6869* (2013.01); *B01L 2200/0663* (2013.01); *B01L 2300/0645* (2013.01); *B01L 2300/0896* (2013.01); *B01L 2400/0415* (2013.01); *B01L 2400/086* (2013.01); *C12Q 2565/631* (2013.01)

(58) Field of Classification Search
CPC .............................................. B01L 2200/0663
See application file for complete search history.

(56) References Cited

U.S. PATENT DOCUMENTS

| | | |
|---|---|---|
| 6,447,663 B1 | 9/2002 | Lee et al. |
| 6,905,586 B2 | 6/2005 | Lee et al. |
| 7,468,271 B2 | 12/2008 | Golovchenko et al. |
| 8,105,471 B1 | 1/2012 | Han et al. |
| 8,652,779 B2 | 2/2014 | Turner et al. |
| 9,644,236 B2 | 5/2017 | Kawai et al. |
| 1,020,264 A1 | 2/2019 | Taniguchi et al. |
| 2002/0046953 A1 | 4/2002 | Lee et al. |

(Continued)

FOREIGN PATENT DOCUMENTS

| | | |
|---|---|---|
| CN | 101046458 A | 10/2007 |
| CN | 102180440 A | 9/2011 |

(Continued)

OTHER PUBLICATIONS

Chen, et al., A novel nanofabrication technique for the array of Nanogap electrodes, Japanese Journal of Applied Physics, Japan Society of Applied physics, JP, 2006, 45(6):5531-5534.

(Continued)

*Primary Examiner* — Paul S Hyun
(74) *Attorney, Agent, or Firm* — Levine Bagade Han LLP

(57) ABSTRACT

The present disclosure provides methods and structures for systems which can linearize and capture a nucleic acid molecule (e.g., DNA) for re-measurement of the nucleic acid molecule or other polymer prior to detection of the polymer. The structures may allow for quick exchange between different samples or other reagents.

18 Claims, 12 Drawing Sheets

(56) References Cited

U.S. PATENT DOCUMENTS

| | | |
|---|---|---|
| 2002/0081744 A1 | 6/2002 | Chan et al. |
| 2002/0168671 A1 | 11/2002 | Burns et al. |
| 2003/0052006 A1 | 3/2003 | Noca et al. |
| 2003/0075445 A1 | 4/2003 | Woudenberg et al. |
| 2003/0104428 A1 | 6/2003 | Branton et al. |
| 2003/0207326 A1 | 11/2003 | Su et al. |
| 2004/0124084 A1 | 7/2004 | Lee et al. |
| 2004/0161708 A1 | 8/2004 | Nagase et al. |
| 2005/0051768 A1 | 3/2005 | Kim et al. |
| 2005/0084865 A1 | 4/2005 | Yu et al. |
| 2005/0112860 A1 | 5/2005 | Park et al. |
| 2006/0011480 A1 | 1/2006 | Sano et al. |
| 2006/0071209 A1 | 4/2006 | Flory et al. |
| 2006/0154399 A1 | 7/2006 | Sauer et al. |
| 2006/0275911 A1* | 12/2006 | Wang ............... C12Q 1/6825 436/106 |
| 2007/0171714 A1 | 7/2007 | Wu et al. |
| 2007/0183198 A1 | 8/2007 | Otsuka et al. |
| 2008/0077607 A1 | 3/2008 | Gatawood et al. |
| 2008/0119366 A1 | 5/2008 | Sauer et al. |
| 2008/0215252 A1 | 9/2008 | Kawai et al. |
| 2008/0248561 A1 | 10/2008 | Golovchenko et al. |
| 2009/0229854 A1 | 9/2009 | Fredenberg et al. |
| 2009/0283412 A1 | 11/2009 | Sansinena et al. |
| 2009/0305273 A1* | 12/2009 | Cao ............... B01L 3/502761 435/6.14 |
| 2010/0267158 A1 | 10/2010 | Chou et al. |
| 2011/0171634 A1* | 7/2011 | Xiao ............... C12Q 1/6825 435/6.1 |
| 2011/0179852 A1 | 7/2011 | Polonsky et al. |
| 2011/0193183 A1 | 8/2011 | Agarwal et al. |
| 2012/0184047 A1 | 7/2012 | Jonsson et al. |
| 2013/0157271 A1 | 6/2013 | Coursey et al. |
| 2013/0264207 A1 | 10/2013 | Ju et al. |
| 2013/0334047 A1 | 12/2013 | Jeong et al. |
| 2014/0008225 A1 | 1/2014 | Jeon et al. |
| 2014/0103945 A1 | 4/2014 | Eid et al. |
| 2014/0202857 A1 | 7/2014 | Valbusa et al. |
| 2014/0273186 A1 | 9/2014 | Oxenrider |
| 2014/0364324 A1 | 12/2014 | Turner et al. |
| 2015/0107996 A1 | 4/2015 | Chen |
| 2015/0111759 A1 | 4/2015 | Ju et al. |
| 2015/0132756 A1 | 5/2015 | Peter et al. |
| 2015/0310228 A1 | 10/2015 | Benz et al. |
| 2015/0323490 A1* | 11/2015 | Luan ............... B82Y 30/00 324/425 |
| 2016/0048690 A1 | 2/2016 | Tanishima et al. |
| 2017/0131237 A1 | 5/2017 | Ikeda |
| 2017/0144158 A1 | 5/2017 | Taniguchi |
| 2017/0146510 A1 | 5/2017 | Ikeda et al. |
| 2017/0146511 A1 | 5/2017 | Taniguchi et al. |
| 2018/0023132 A1 | 1/2018 | Kawai et al. |

FOREIGN PATENT DOCUMENTS

| | | |
|---|---|---|
| CN | 102914395 A | 2/2013 |
| EP | 1419112 A1 | 5/2004 |
| EP | 2573554 A1 | 3/2013 |
| JP | 62-194673 A | 8/1987 |
| JP | 6437640 A | 2/1989 |
| JP | 04-302151 A | 10/1992 |
| JP | H04302151 A | 10/1992 |
| JP | 10283230 A | 10/1998 |
| JP | 2003507026 A | 2/2003 |
| JP | 2004303162 A | 10/2004 |
| JP | 2005501234 A | 1/2005 |
| JP | 2008146538 A | 6/2008 |
| JP | 4289938 B2 | 7/2009 |
| JP | 2010510476 A | 4/2010 |
| JP | 4719906 B2 | 7/2011 |
| JP | 2012118709 A | 6/2012 |
| JP | 2013090576 A | 5/2013 |
| JP | 2013518283 A | 5/2013 |
| JP | 2013519074 A | 5/2013 |
| JP | 2013215725 A | 10/2013 |
| JP | 2014173936 A | 9/2014 |
| KR | 102014003155 | 3/2014 |
| TW | 200619614 A | 6/2006 |
| TW | 200637916 A | 11/2006 |
| TW | 200907068 A | 2/2009 |
| TW | 201013179 A | 4/2010 |
| TW | 201100796 A | 1/2011 |
| WO | WO-03042396 A2 | 5/2003 |
| WO | WO-2008071982 A3 | 7/2008 |
| WO | WO-2010111605 A2 | 9/2010 |
| WO | WO-2010111605 A3 | 11/2010 |
| WO | WO-2012009578 A2 | 1/2012 |
| WO | WO-2012009578 A3 | 4/2012 |
| WO | WO-2013016486 A1 | 1/2013 |
| WO | WO-2013066456 A2 | 5/2013 |
| WO | WO-2013074546 A1 | 5/2013 |
| WO | WO-2013066456 A3 | 7/2013 |
| WO | WO-2013115185 A1 | 8/2013 |
| WO | WO-2014027580 A1 | 2/2014 |
| WO | WO-2015028885 A2 | 3/2015 |
| WO | WO-2015042200 A1 | 3/2015 |
| WO | WO-2015028885 A3 | 4/2015 |
| WO | WO-2015028886 A3 | 5/2015 |
| WO | WO-2015125920 A1 | 8/2015 |
| WO | WO-2015167019 A1 | 11/2015 |
| WO | WO-2015170782 A1 | 11/2015 |
| WO | WO-2015170783 A1 | 11/2015 |
| WO | WO-2015170784 A1 | 11/2015 |
| WO | WO-2016206593 A1 | 12/2016 |
| WO | WO-2017061129 A1 | 4/2017 |
| WO | WO-2017179581 A1 | 10/2017 |
| WO | WO-2017189930 A1 | 11/2017 |
| WO | WO-2018025887 A1 | 2/2018 |
| WO | WO-2019065904 A1 | 4/2019 |

OTHER PUBLICATIONS

El-Ali, et al., Simulation and experimental validation of a SU-8 based PCR themorcycler chp with integrated heaters and temperature sensor, Sensors and Actuators A, 110, 2004, pp. 3-10.

Hashioka, et al, Metal nanogap devices fabricated by conventional photolithography and their application to deoxyribose nucleic acid analysis, Journal of Vacuum Science & Technology B: microelectronics; Materials, Processing and Phenomena, 2003, 21(6):2937-40.

Tsutsui, et al., Formation and self-breaking mechanism of stable atom-sized junctions, Nano Letters, 2008, 8(1):345-349.

Axopatch 2008 Patch Clamp: Theory and Operation, Axon Instruments, Inc., Mar. 1999.

Chen, et al., Probing Single DNA Molecule Transport Using Fabricated Nanopores, Nano Letters, 2004, 4(11):2293-2298.

Armbrust et al. Clearing the clouds away from the true potential and obstacles posed by this computing capability. Communications of the ACM 53(4):50-58 (Apr. 2010).

Furuhashi et al. Denaturation of DNAs in a nanofluidic channel by micro-heating method. The 74th Annual Meeting of the Japan Society of Applied Physics Lecture Papers p. 12-295 (Aug. 2013).

Furuhashi et al. Denature of double-stranded DNAs by a micro-heating method. Proceedings of the 60th Spring Science Lecture Meeting of the Japan Society of Applied Physics, p. 12-356, (Mar. 2013).

Garcia-Lekue et al. Plane-wave-based electron tunneling through Au nanojunctions: Numerical calculations. Physical Review B 82:035410 (2010). 9 pages.

Healy et al. Fabrication and characterization of nanopores with insulated transverse nanoelectrodes for DNA sensing in salt solution. Electrophoresis 33(23) (Dec. 2012). doi: 10.1002/elps. 201200350. 15 pages.

PCT/JP2015/063963 International Preliminary Report on Patentability dated Nov. 8, 2016.

Feng et al. "Nanopore-based Fourth-generation DNA Sequencing Technology" Genomics, Proteomics & Bioinformatics. 2015; 13(1):4-16, p. 5, col2, para 3.

(56) References Cited

OTHER PUBLICATIONS

Fuller et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.
Schreiber et al. "Error rates for nanopore discrimination among cytosine, methylcytosine, and hydroxymethylcytosine along individual DNA strands" PNAS, 2013; 11 0(47): 18910-18915, p. 18910, col. 2, para 3.
Co-pending U.S. Appl. No. 15/937,327, filed Mar. 27, 2018.
Suga et al. Influence of electrode size on resistance switching effect in nanogap junctions, Applied Physics Letter, 2010, 97(7):73118, 4 pages. Epub Aug. 20, 2010.
Co-pending U.S. Appl. No. 16/266,363, filed Feb. 4, 2019.
Anima et al. Fabrications of insulator-protected nanometer-sized electrode gaps. Journal of Applied Physics 115:114310 (2014). 6 pages. doi: 10.1063/1.4869135.
Co-pending U.S. Appl. No. 16/156,755, filed Oct. 10, 2018.
Co-pending U.S. Appl. No. 16/169,756, filed Oct. 24, 2018.
Co-pending U.S. Appl. No. 16/178,924, filed Nov. 2, 2018.
Co-pending U.S. Appl. No. 16/234,908, filed Dec. 28, 2018.
Ohshiro et al. Supplementary Information for Single-Molecule Electrical Random Resequencing of DNA and RNA. Scientific Reports 2, Article No. 501 (Jul. 10, 2012). 23 pages. doi:10.1038/srep00501.
Tsutsui et al. Electrical Detection of Single-Methylcytosines in a DNA Oligomer. J Am Chem Soc 133(23): 9124-9128 (May 11, 2011). DOI: 10.1021/ja203839e.
Tsutsui et al. Supplementary Information for Identifying Single Nucleotides by Tunneling Current. Nature Nanotechnology 5:286-290 (Mar. 21, 2010). doi: 10.1038/NNANO.2010.42.
Tsutsui et al. Supporting Information for Electrical Detection of Single-Methylcytosines in a DNA Oligomer. J Am Chem Soc 133(23): 9124-9128 (May 11, 2011). DOI: 10.1021/ja203839e.

* cited by examiner

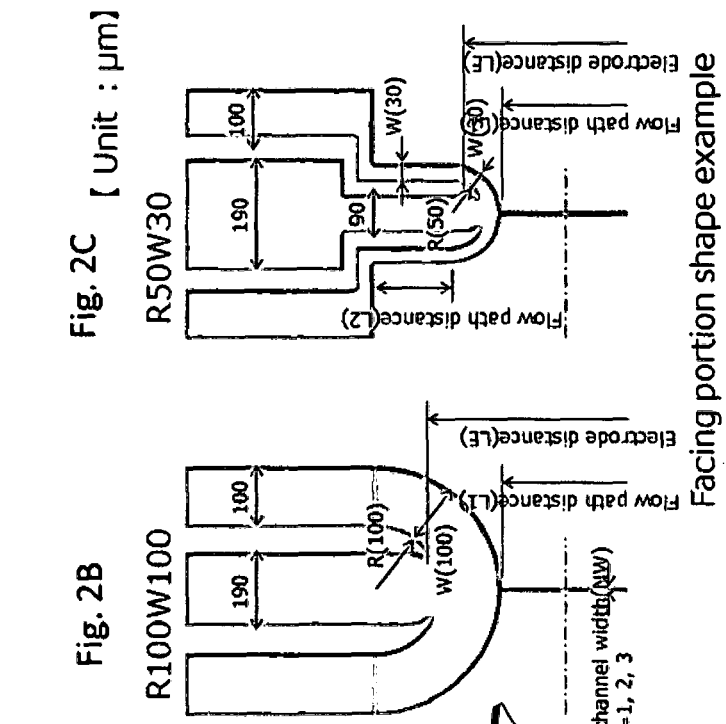
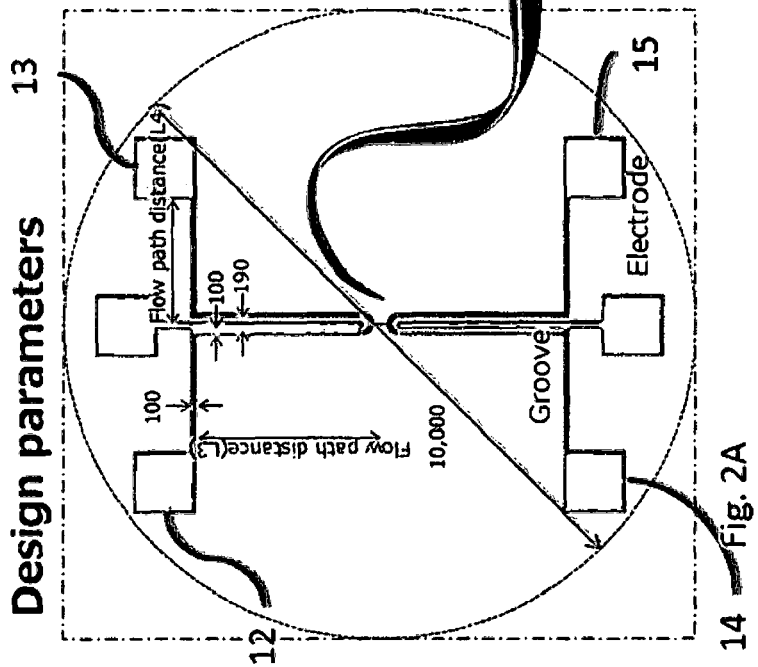
Fig. 2A, Fig. 2B, Fig. 2C

Layout Example
(PB_R50W10LB60)

Overall view

DEVICES, SYSTEMS AND METHODS FOR LINEARIZATION OF POLYMERS

CROSS-REFERENCE

This application is a continuation of International Patent Application No. PCT/JP2015/063963, filed May 8, 2015, which claims priority to U.S. Provisional Patent Application Ser. No. 61/990,589, filed May 8, 2014, each of which is entirely incorporated herein by reference.

DESCRIPTION OF THE RELATED ART

Nanopores may be useful for determining the sequence of a nucleic acid molecule, such as a deoxyribonucleic acid (DNA) or ribonucleic acid (RNA) molecule. The determination of the sequence of a nucleic acid molecule may provide various benefits, such as aiding in diagnosing and/or treating a subject. For example, the nucleic acid sequence of a subject may be used to identify, diagnose and potentially develop treatments for genetic diseases.

SUMMARY OF THE INVENTION

In order to effectively utilize the nanoelectrodes, it may be necessary to linearize a nucleic acid molecule, such as a deoxyribonucleic acid (DNA) or ribonucleic acid (RNA) molecule. Nanopore and nanochannel systems are quite easily clogged due to the very small size of the pores and or channels. It may thus be desirable to filter or further filter the sample so as to prevent clogging of the nanoelectrodes system. The fluidic channels of a nanopore or nanoelectrodes system may have a volume which is quite large relative to the flow capacity of the nanopore(s) or nanoelectrode channel(s). It may also be desirable to allow for sample and or regent exchanges at rates faster than achievable utilizing flow through the nanopore or nanoelectrode channels.

The present disclosure provides nanoelectrode systems which may be used for sensing and/or sequencing a nucleic acid molecule, such as deoxyribonucleic acid (DNA) or ribonucleic acid (RNA), or sequencing and/or sensing other biopolymers and detection and identification of other molecules. A nucleic acid sequencing device or system of the present disclosure can include tunneling nanoelectrodes, particularly adjustable tunneling nanoelectrodes, which may be used for determining the sequence of a nucleic acid molecule. The nucleic acid molecule can be single stranded or double stranded.

An aspect of the present disclosure provides a system for sequencing a biopolymer, comprising: a nanochannel having a detection region for detecting the biopolymer or portion thereof upon flow of the biopolymer through the detection region; and a first entropic trapping component and second entropic trapping component disposed in or adjacent to the nanochannel, wherein (i) the first entropic trapping component is operable to linearize the biopolymer upon flow of the biopolymer through the first entropic trapping component and towards a first side of the detection region, and (ii) the second entropic trapping component is operable to linearize the biopolymer upon flow of the biopolymer through the second entropic trapping component and towards a second side of the detection region, which first side is different from the second side.

In some embodiments of aspects provided herein, the first and/or second entropic trapping component comprises nanopillars with gap spacing of less than about 50 nanometers. In some embodiments of aspects provided herein, the first and/or second entropic trapping component permits movement of the biopolymer back and forth in the nanochannel. In some embodiments of aspects provided herein, the system further comprises a fluid channel adjacent to an end of the nanochannel, which fluid channel is larger in cross-section than the nanochannel. In some embodiments of aspects provided herein, the first and/or second entropic trapping component is disposed in the fluid channel. In some embodiments of aspects provided herein, the fluid channel is at least five times larger in cross-section than the nanochannel. In some embodiments of aspects provided herein, the fluid channel is at least ten times larger in cross-section than the nanochannel. In some embodiments of aspects provided herein, the fluid channel and the nanochannel are integrated in a substrate. In some embodiments of aspects provided herein, the system further comprises an additional fluid channel adjacent to an additional end of the nanochannel, wherein the additional fluid channel is larger in cross-section than the nanochannel. In some embodiments of aspects provided herein, the fluid channel is arranged to permit a fluid containing the biopolymer to flow around the detection region. In some embodiments of aspects provided herein, the first and/or second entropic trapping component is configured to entropically trap and concentrate the biopolymer. In some embodiments of aspects provided herein, the detection region comprises a pair of electrodes that are spaced apart by a gap, and the pair of electrodes is operable to detect an electrical current across the gap upon flow of the biopolymer through the gap. In some embodiments of aspects provided herein, the first and/or second entropic trapping component permits flow of the biopolymer towards the detection region at a greater flow rate than away from the detection region. In some embodiments of aspects provided herein, the first and/or second entropic trapping component comprises a plurality of pillars that are arranged so as to separate (i) a strand of the biopolymer or (ii) strands of the biopolymer from non-biopolymer moieties. In some embodiments of aspects provided herein, the first entropic trapping component is in the nanochannel, and the first entropic trapping component includes an increase in cross-section of the nanochannel followed by a decrease in cross-section of the nanochannel towards the detection region. In some embodiments of aspects provided herein, the second entropic trapping component includes an increase in cross-section of the nanochannel followed by a decrease in cross-section of the nanochannel away from the detection region. In some embodiments of aspects provided herein, in the first entropic trapping component, the increase in cross-section is abrupt relative to the decrease in cross-section. In some embodiments of aspects provided herein, in the second entropic trapping component, the decrease in cross-section is abrupt relative to the increase in cross-section. In some embodiments of aspects provided herein, the first entropic trapping component is upstream of the detection region and the second entropic trapping component is downstream of the detection region, or vice versa.

Another aspect of the present disclosure provides a method for biopolymer sequencing, comprising: (a) subjecting a biopolymer to flow from a fluid channel through a nanochannel, wherein the fluid channel has a larger cross-section than the nanochannel, and wherein the nanochannel includes a detection region for detecting the biopolymer or portion thereof upon flow of the biopolymer through the detection region; (b) upon flow of the biopolymer from the fluid channel to or through the nanochannel, linearlizing the biopolymer using an entropic trapping component in or adjacent to the nanochannel; (c) measuring signals indicative of the biopolymer or portion thereof in the detection region; and (d) using the signals measured in (c) to generate a sequence of the biopolymer.

In some embodiments of aspects provided herein, (a) comprises flowing a fluid containing the biopolymer around the detection region. In some embodiments of aspects provided herein, (a) comprises subjecting a fluid containing the biopolymer to pressure-driven flow in the fluid channel. In some embodiments of aspects provided herein, the fluid flows through the nanochannel under electrokinetic or electroosmotic-driven flow. In some embodiments of aspects provided herein, the entropic trapping component comprises nanopillars with gap spacing of less than about 50 nanometers. In some embodiments of aspects provided herein, the entropic trapping component permits movement of the biopolymer back and forth in the nanochannel. In some embodiments of aspects provided herein, the entropic trapping component is disposed in the fluid channel. In some embodiments of aspects provided herein, the detection region comprises a pair of electrodes that are spaced apart by a gap, the signals are electrical current, and the pair of electrodes detects the electrical current across the gap upon flow of the biopolymer through the gap. In some embodiments of aspects provided herein, the entropic trapping component flows the biopolymer towards the detection region at a greater flow rate than away from the detection region. In some embodiments of aspects provided herein, the fluid channel is at least five times larger in cross-section than the nanochannel. In some embodiments of aspects provided herein, the fluid channel is at least ten times larger in cross-section than the nanochannel. In some embodiments of aspects provided herein, the entropic trapping component comprises a plurality of pillars that are arranged so as to separate (i) a strand of the biopolymer or (ii) strands of the biopolymer from non-biopolymer moieties. In some embodiments of aspects provided herein, the fluid channel and the nanochannel are integrated in a substrate. In some embodiments of aspects provided herein, the method further comprises (i) reversing a direction of flow of the biopolymer through the nanochannel and (ii) using the pair of electrodes to measure electrical current across the gap upon flow of the biopolymer through the gap. In some embodiments of aspects provided herein, the entropic trapping component includes an increase in cross-section of the nanochannel followed by a decrease in cross-section of the nanochannel towards the detection region. In some embodiments of aspects provided herein, the increase in cross-section is abrupt relative to the decrease in cross-section. In some embodiments of aspects provided herein, the entropic trapping component entropically traps and concentrates the biopolymer.

Another aspect of the present disclosure provides a system for biopolymer sequencing, comprising: a substrate including a fluid channel and at least one nanochannel in fluid communication with the fluid channel, wherein the fluid channel has a larger cross-section than the at least one nanochannel; a detector in sensing communication with the at least one nanochannel, wherein the detector detects a biopolymer as the biopolymer passes through the at least one nanochannel; and a biopolymer storage member in fluid communication with the detector.

In some embodiments of aspects provided herein, the detector comprises at least one pair of nanoelectrodes intersecting the at least one nanochannel. In some embodiments of aspects provided herein, the biopolymer storage member is above and/or below the least one nanoelectrode pair.

Another aspect of the present disclosure provides a system for biopolymer sequencing, comprising: a substrate including a fluid channel and at least one nanochannel in fluid communication with the fluid channel, wherein the fluid channel has a larger cross-section than the at least one nanochannel; a biopolymer capturer that directs a biopolymer from the fluid channel into or through the at least one nanochannel; a detector in sensing communication with the at least one nanochannel, wherein the detector detects the biopolymer as the biopolymer passes through the at least one nanochannel; and a biopolymer linearization member that linearizes the biopolymer upon flow into or through the at least one nanochannel.

In some embodiments of aspects provided herein, the detector comprises at least one pair of nanoelectrodes intersecting the at least one nanochannel. In some embodiments of aspects provided herein, the biopolymer linearization member comprises a plurality of pillars. In some embodiments of aspects provided herein, the plurality of pillars is arranged so as to have a noncontinuous gradient of pillar sizes. In some embodiments of aspects provided herein, the plurality of pillars is arranged so as to have a noncontinuous gradient of pillar separation distances. In some embodiments of aspects provided herein, the plurality of pillars is arranged so as to have gaps of greater than twice a pillar separation distance between sets of pillars. In some embodiments of aspects provided herein, individual pillars of the plurality of pillars are spaced non-uniformly across a cross-section of the fluid channel. In some embodiments of aspects provided herein, the biopolymer capturer includes a pair of electrodes disposed at each end of the at least one nanochannel.

Another aspect of the present disclosure provides a system for biopolymer detection, comprising: a substrate including a fluid channel and at least one nanochannel in fluid communication with the fluid channel, wherein the fluid channel has a larger cross-section than the at least one nanochannel; a detector in sensing communication with the at least one nanochannel, wherein the detector detects the biopolymer as the biopolymer passes through the at least one nanochannel; and entropic trapping components in or adjacent to the at least one nanochannel.

In some embodiments of aspects provided herein, the detector comprises at least one pair of nanoelectrodes intersecting the at least one nanochannel.

Another aspect of the present disclosure provides a system for biopolymer concentration, comprising: a substrate including a fluid channel and at least one nanochannel in fluid communication with the fluid channel, wherein the fluid channel has a larger cross-section than the at least one nanochannel; and an entropic trapping component comprising a plurality of pillars in the fluid channel, wherein individual pillars of the plurality of pillars are spaced non-uniformly across a cross-section of the fluid channel.

Another aspect of the present disclosure provides a system for biopolymer detection, comprising a substrate including a fluid channel and a plurality of nanochannels in fluid communication with the fluid channel, wherein the fluid channel has a larger cross-section than the plurality of nanochannels, wherein the plurality of nanochannels (i) have different cross-sections or (ii) inlets with non-uniform spacings in the fluid channel.

In some embodiments of aspects provided herein, each of the plurality of nanochannels has a detection region for detecting a biopolymer or portion thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "Fig." herein), of which:

FIGS. 2A-2C illustrate schematic representations of some details of a linearization and filtration system.

DETAILED DESCRIPTION OF THE INVENTION

Figure 1B:
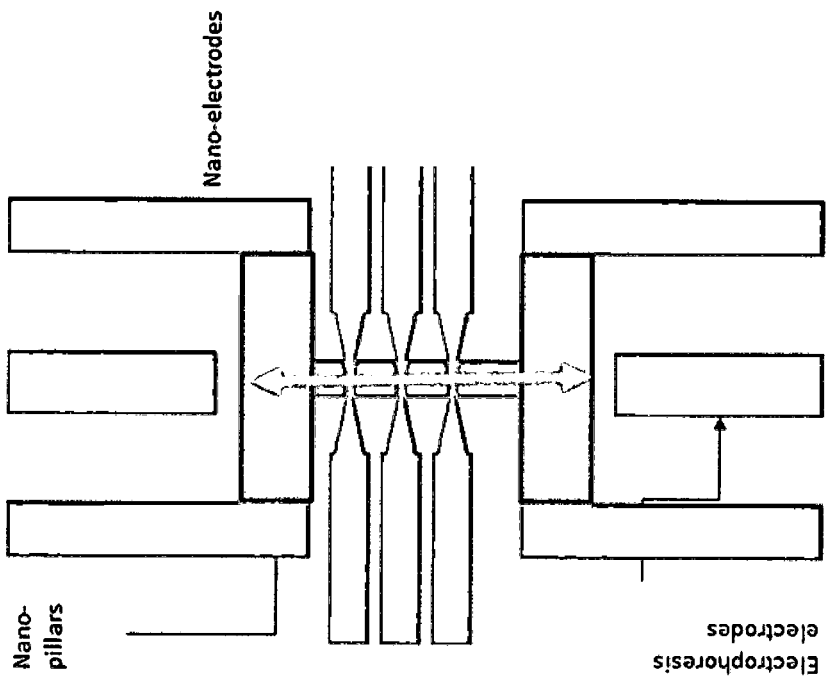
FIGS. 1A-1B illustrate schematic representations of single and multi-nanoelectrode channels.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "gap," as used herein, generally refers to a pore, channel or passage formed or otherwise provided in a material. The material may be a solid state material, such as a substrate. The gap may be disposed adjacent or in proximity to a sensing circuit or an electrode coupled to a sensing circuit. In some examples, a gap has a characteristic width or diameter on the order of 0.1 nanometers (nm) to about 1000 nm. A gap having a width on the order of nanometers may be referred to as a "nano-gap" (also "nanogap" herein). In some situations, a nano-gap has a width that is from about 0.1 nanometers (nm) to 50 nm, 0.5 nm to 30 nm, or 0.5 nm or 10 nm, 0.5 nm to 5 nm, or 0.5 nm to 2 nm, or no greater than 2 nm, 1 nm, 0.9 nm, 0.8 nm, 0.7 nm, 0.6 nm, or 0.5 nm. In some cases, a nano-gap has a width that is at least about 0.5 nm, 0.6 nm, 0.7 nm, 0.8 nm, 0.9 nm, 1 nm, 2 nm, 3 nm, 4 nm, or 5 nm. In some cases, the width of a nano-gap can be less than a diameter of a biomolecule or a subunit (e.g., monomer) of the biomolecule.

The term "electrode," as used herein, generally refers to a material or part that can be used to measure electrical current. An electrode (or electrode part) can be used to measure electrical current to or from another electrode. In some situations, electrodes can be disposed in a channel (e.g., nanogap) and be used to measure the current across the channel. The current can be a tunneling current. Such a current can, be detected upon the flow of a biomolecule (e.g., protein) through the nano-gap. In some cases, a sensing circuit coupled to electrodes provides an applied voltage across the electrodes to generate a current. As an alternative or in addition to, the electrodes can be used to measure and/or identify the electric conductance associated with a biomolecule (e.g., an amino acid subunit or monomer of a protein). In such a case, the tunneling current can be related to the electric conductance.

In some examples, a nanoelectrode pair includes individual nanoelectrodes that are separated by a gap with spacing less than or equal to about 50 nm, 40 nm, 30 nm, 20 nm, 10 nm, 5 nm, 4 nm, 3 nm, 2 nm, 1 nm, or 0.5 nm. A nanoelectrode may have any convenient shape or size and can be comprised of any conductive material. Each electrode of the present disclosure can be fabricated from different materials or from mixtures of materials such as alloys.

The term "nanochannel," as used herein, general refers to a covered trench with at least one pair of nanoelectrodes intersecting the nanochannel. A channel may have any convenient shape or size, in some cases with varying width and depth.

The term "nanopillar," as used herein, generally refers to a protrusion into a fluidic channel (e.g., nanochannel) that provides a flow path for molecular flow with a cross-section that is less than about 50 nm.

The term "biomolecule," as used herein generally refers to any biological material that can be interrogated with an electrical current and/or potential across a nano-gap electrode. A biomolecule can be a nucleic acid molecule, protein, or carbohydrate. A biomolecule can include one or more subunits, such as nucleotides or amino acids. In some examples, a biomolecule is a biopolymer, which is any polymer in an organism and may include DNA, RNA, proteins, lipid chains and polysaccharides. A biopolymer may be a polymer which may be a modified version of a polymer from an organism.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

The term "protein," as used herein, generally refers to a biological molecule, or macromolecule, having one or more amino acid monomers, subunits or residues. A protein containing 50 or fewer amino acids, for example, may be referred to as a "peptide." The amino acid monomers can be selected from any naturally occurring and/or synthesized amino acid monomer, such as, for example, 20, 21, or 22 naturally occurring amino acids. In some cases, 20 amino acids are encoded in the genetic code of a subject. Some proteins may include amino acids selected from about 500 naturally and non-naturally occurring amino acids. In some situations, a protein can include one or more amino acids selected from isoleucine, leucine, lysine, methionine, phenylalanine, threonine, tryptophan and valine, arginine, histidine, alanine, asparagine, aspartic acid, cysteine, glutamine, glutamic acid, glycine, proline, serin and tyrosine.

The term "layer," as used herein, refers to a layer of atoms or molecules on a substrate. In some cases, a layer includes an epitaxial layer or a plurality of epitaxial layers. A layer may include a film or thin film. In some situations, a layer is a structural component of a device (e.g., light emitting diode) serving a predetermined device function, such as, for example, an active layer that is configured to generate (or emit) light. A layer generally has a thickness from about one monoatomic monolayer (ML) to tens of monolayers, hundreds of monolayers, thousands of monolayers, millions of monolayers, billions of monolayers, trillions of monolayers, or more. In an example, a layer is a multilayer structure having a thickness greater than one monoatomic monolayer. In addition, a layer may include multiple material layers (or sub-layers). In an example, a multiple quantum well active layer includes multiple well and barrier layers. A layer may include a plurality of sub-layers. For example, an active layer may include a barrier sub-layer and a well sub-layer.

The term "adjacent" or "adjacent to," as used herein, includes 'next to', 'adjoining', 'in contact with', and 'in proximity to'. In some instances, adjacent to components are separated from one another by one or more intervening layers. For example, the one or more intervening layers can have a thickness less than about 10 micrometers ("microns"), 1 micron, 500 nanometers ("nm"), 100 nm, 50 nm, 10 nm, 1 nm, or less. In an example, a first layer is adjacent to a second layer when the first layer is in direct contact with the second layer. In another example, a first layer is adjacent to a second layer when the first layer is separated from the second layer by a third layer.

The term "substrate," as used herein, refers to any workpiece on which film or thin film formation is desired. A substrate includes, without limitation, silicon, germanium, silica, sapphire, zinc oxide, carbon (e.g., graphene), SiC, AlN, GaN, spinel, coated silicon, silicon on oxide, silicon carbide on oxide, glass, gallium nitride, indium nitride, titanium dioxide and aluminum nitride, a ceramic material (e.g., alumina, AlN), a metallic material (e.g., molybdenum, tungsten, copper, aluminum), and combinations (or alloys) thereof. A substrate can include a single layer or multiple layers.

In some cases, deoxyribonucleic acid (DNA) forms a ball due in part to self hybridization forming secondary structure, and may do so even under nominally nondenaturing conditions. DNA samples are routinely filtered with spin columns with pore sizes of from 10 to 20 μm to capture contaminants which may be in a solution with the desired DNA. DNA samples are routinely filtered (to capture the DNA and remove the fluid in which they are solubilized) using filters with pores sizes of 0.45 μm or 0.22 μm to capture DNA; as the channel input may be of a similar size, a DNA strand may never enter into the channel. Thus in some embodiments, it may be desirable to linearize the DNA or other biopolymer prior to allowing the DNA or other biopolymer to interact with the entrance of the nanochannel. The DNA or other biopolymer may be entrapped utilizing an entropic entrapment device, which may allow the DNA or other biopolymer to be retained for further analysis. The nanochannel may comprise a detection region for sensing or detecting the biopolymer (e.g., DNA). The detection region may include one or more nanoelectrode pairs (e.g., at least 2, 3, 4, 5, 6, 7, 8, 9, or 10 nanoelectrode pairs), which may serve as tunneling current detectors. As an alternative or in addition to, the detection region may include or be in sensing communication with or other types of detectors, such as optical detectors (e.g., florescent optical detectors), conductivity detectors, capacitive detectors, electrochemical detectors, or any other appropriate detector, which may be utilized to sense the biopolymer.

A system for sequencing or detecting DNA or other biopolymers may be effectuated by a device with one or more fluidic nanochannels which may incorporate nanoelectrode pairs that intersect a nanochannel or other detectors which may detect biopolymers and or monomers of the biopolymer. In some embodiments, nanogap tunneling electrodes may be fabricated on a substrate.

A substrate may be a chip of a semiconductor material such as, for example, silicon, germanium, and the like; an isolating material such as a plastic material, glass, and the like, or a metal or an alloy of metals. If the substrate is made of a metal, the electrodes may be electrically isolated from the substrate. In some embodiments, the substrate is polyamide, SiN, or other appropriate dielectric material.

In some embodiments the device may be fabricated, at least in part, in a microelectromechanical systems (MEMS) facility. The device may include additional electronic circuitry, which may be fabricated in a standard complementary metal-oxide semiconductor (CMOS) facility.

The present disclosure provides devices, systems and methods for sensing or detecting biopolymers. Such devices, systems and methods can be used to sequence biopolymers, such as DNA. Biopolymers other than DNA may be sequenced. In some embodiments biopolymers such as RNA, proteins, lipid polymers and polysaccharides may be sequenced. In this disclosure is implied that any mention of DNA can be replaced by another biopolymer.

Sample volumes which may reasonably be pipetted may be far larger than can be flowed through a nanochannel in a reasonable time frame. Pipetting of volumes of less than one microliter is considered to have significant variability when using standard pipettors, thus restricting minimum volumes. In a system having a linear fluidic flow rate of one micrometer (micron) per second through a one micron by one micron by one micron (box) channel, it may take over 31 years for a one microliter sample to flow through the channel. A flow rate of one micron per second may be close to a maximum usable flow rate during detection. Flushing out with pressure may also take too long. For example if a nanochannel was one micron in diameter and 10 microns long at 10 psi (68940 Pa) it may take almost 100 minutes for one microliter to flow through.

Thus, it may be desirable to concentrate and capture DNA or other biopolymers which may be contained in a sample volume, and to allow for quick exchanges of samples, wash buffers and other reagents which may be desired between samples in order to prevent cross contamination between samples.

In a nanopore or nanochannel system which may be used for DNA sequencing, the lifetime of a nanopore and nanochannel system may typically be limited by clogging of a nanopore or nanochannel, either by secondary structure of DNA, or by contaminating particulate material which has not been removed by prior filtration. Thus, it may be desirable to linearize DNA strand prior to introduction to a nanopore or nanochannel. In some embodiments, a solution is allowed to flow past a nanopore or nanochannel, while capturing DNA or other moieties of interest and causing them to flow through the nanopore or nanochannel. A solution containing DNA may be filtered or further filtered. Two or more of these features may be combined in a single device.

Figure 1A:
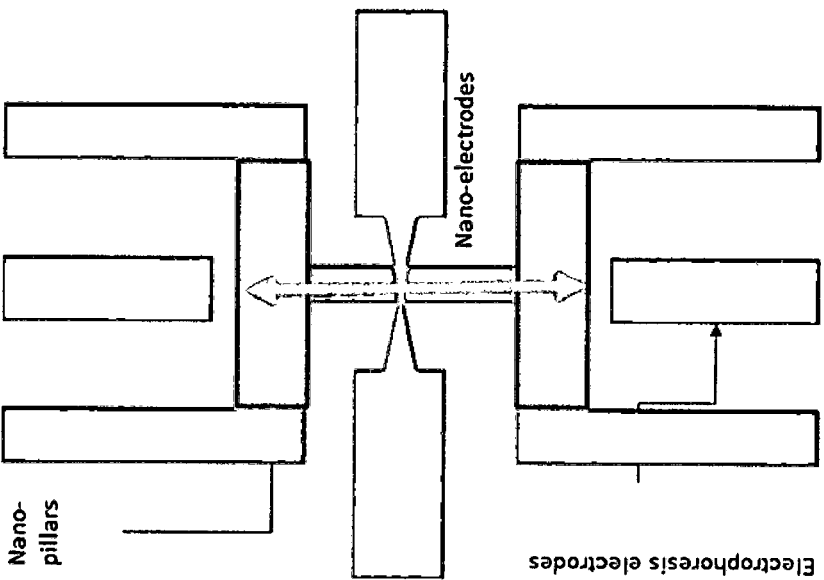

FIG. 1A schematically illustrates a biopolymer capturer system which combines a set on nanopillars in a pressure driven flow micro branch of a fluidics subsystem, which may be used to linearize DNA prior to being directed into a nano branch of the fluidics system. Most of the fluid may continue past the nano branch utilizing hydrodynamic flow, while DNA may be captured by an orthogonal flow, which may be an electrokinetic flow and or electroosmostic flow which may result from an electric potential which may extend across the width of the hydrodynamic flow and through the nano branch of the fluidics system. In some embodiments pressure driven flow may be used to move DNA through a nanochannel. There may be a second larger channel at an end of a nano branch of a fluidics system opposite to a channel wherein a sample may be introduced to the system and thence into the nano branch of the fluidics system. Am electric field may be used to create an electrokinetic flow may be further extended across this second larger channel.

A second larger channel may be utilized to remove sample DNA, after passing through a nano branch of a biopolymer capturer system, and or to introduce and remove different reagents to or from an electrode or nano branch of a fluidics system. A second electrode is shown on the far side of a second channel so as to cause an electric field to be impressed across a first larger fluidics channel, through the nano branch of the fluidics system, and across the second larger channel.

As schematically illustrated in FIG. 1B, multiple sets or pairs of electrodes or other detectors may be utilized, so as to allow multiple reads on a same strand of DNA without having to cause the DNA to translocate back and forth through a nanopore or nanochannel with a single detector. A detector may detect signals that are indicative of a biopolymer or portion thereof. The detector may be an electrical current (e.g., tunneling current) detector, an optical detector, or an ion current detector, wherein multiple sets of electrodes may be configured along a nanochannel with appropriately sized nanopores so as to measure currents which passes through each nanopore as a DNA strand translocates through pores.

In some embodiments, multiple nanochannels may be configured to be located between two larger channels in a fluidic system, allowing for simultaneous measurement of several strands of DNA. In further embodiments, an entrance to a channel may be configured so as to have variable spacings between channels, and or various sizes of entrance apertures such that DNA strands may be uniformly distributed between channels, rather than being concentrated into a single channel or into the first few of several channels by an electrophoretic field. Spacings and or sizes may be configured so as to take into consideration electrokinetically induced migration rate resulting from an electric field, a width of the channel, a concentration of DNA, a pressure induced hydrodynamic flow rate of a larger channel, and an ionic concentration of the solution, among other factors. Hydrodynamic flow rate, electric field, DNA concentration, and ionic solution concentration may be varied as needed to consider others of the same set which may not be easily varied.

As schematically illustrated in FIG. 2A, fluid which contains the sample DNA or other sample moieties of interest may be introduced to the fluidic system, for example through an input port 12, and may then flow through a large fluidic channel to and in contact with an upper electrode, around the electrode, and to an output port 13. Similarly an additional fluid may be flowed from lower input port 14 to lower output port 15 through a second large channel, in order to remove sample material, clean the channel, or stabilize, modify or change surface conditions of the channels or electrode.

As schematically illustrated in FIG. 2B, the large fluidic channel may have a channel width of less than 10 µm, of between 10 µm and 30 µm, of between 30 µm and 50 µm, of between 50 µm and 100 µm, or greater than 100 µm. An electrode may be 10 µm in width, but may be of other widths, particularly as needed if multiple nanochannels are a part of the fluidic system or as needed to achieve desired system density. The tip of the electrode may be less than 50 µm, or between 50 µm and 100 µm, or greater than 100 µm, and may have a smooth radius, or may have a more complicated curve, particularly as needed to result in uniform distribution of DNA into multiple nanochannels.

As schematically illustrated in FIG. 2C, a large fluidic channel(s) need not be of uniform width (or thickness). As shown in FIG. 2C, the large fluidic channel may be stepped down in width from 100 µm to 30 µm, and the fluidic flow may be configured to conform in an accompanying change in the width of the electrode, which in this case is reduced from 190 µm to 90 µm. The electrode size may be decreased gradually; similarly the channel width of the large channel may be reduced in a gradual manner, or may be reduced in several steps.

As shown in FIG. 2B and FIG. 2C, a dielectric layer may be utilized to prevent fluidic contact except where desired at the tip of the electrode.

A large channel depth may be less than 0.5 µm, from 0.5 µm to 1.0 µm, from 1.0 µm to 5 µm, from 5 µm to 10 µm, greater than 10 µm. A nanochannel, which may have tunneling electrodes constructed so as to detect DNA or other moieties of interest as they translocate through a nanochannel, may be less than 1.0 µm in width, from 1.0 µm to 2.0 µm in width, from 2.0 µm to 3.0 µm in width, or greater than 3.0 µm in width. A channel may be of a same depth as a large channel(s), or may be of a smaller depth. A depth of a nanochannel may be uniform, or may be varied, and may be varied so as to maximize opportunity for interaction of DNA or other moieties with tunneling electrodes or other detectors. Similarly a width of a nanochannel may be uniform, or may be varied. In particular, a width or depth of a nanochannel may be reduced in an area of a detector so as to maximize the opportunity of interaction with the detector(s). In some embodiments, additional electrodes in a vertical axis may be utilized within a nanochannel so as to influence a position of DNA or other moiety in a vertical axis. An adjustment of a position of a DNA may be made so as to better align the DNA or other moiety of interest with a detector, for example pulling DNA to a top of a channel when a detector, which may be a pair of tunneling electrodes, may be positioned at or close to a top of a channel. Electrodes which may be utilized to influence a vertical position of DNA or other moieties of interest may be positioned so as to be sufficiently far from tunneling electrodes so as to not unduly influence any measurements taken by the tunneling electrodes, but may also be positioned sufficiently close so as to prevent Brownian motion from allowing DNA or other moieties of interest to migrate vertically away from the electrodes. In some embodiments more than one pair of vertical electrodes may be utilized. For example one may be utilized to collect and concentrate DNA or other moieties from wherever in the vertical axis of the DNA or other moieties may be located to a known location very close to an upper vertical electrode, and a second pair of vertical electrodes may be utilized to pull DNA down so as to allow interaction with tunneling electrodes, which may be positioned so as to be close to a top, but not in contact. A field strength of electrodes may be of sufficient strength as to appropriately influence a position of DNA or other moieties, but insufficient to cause cessation of movement by DNA or other moieties.

Figure 3A:
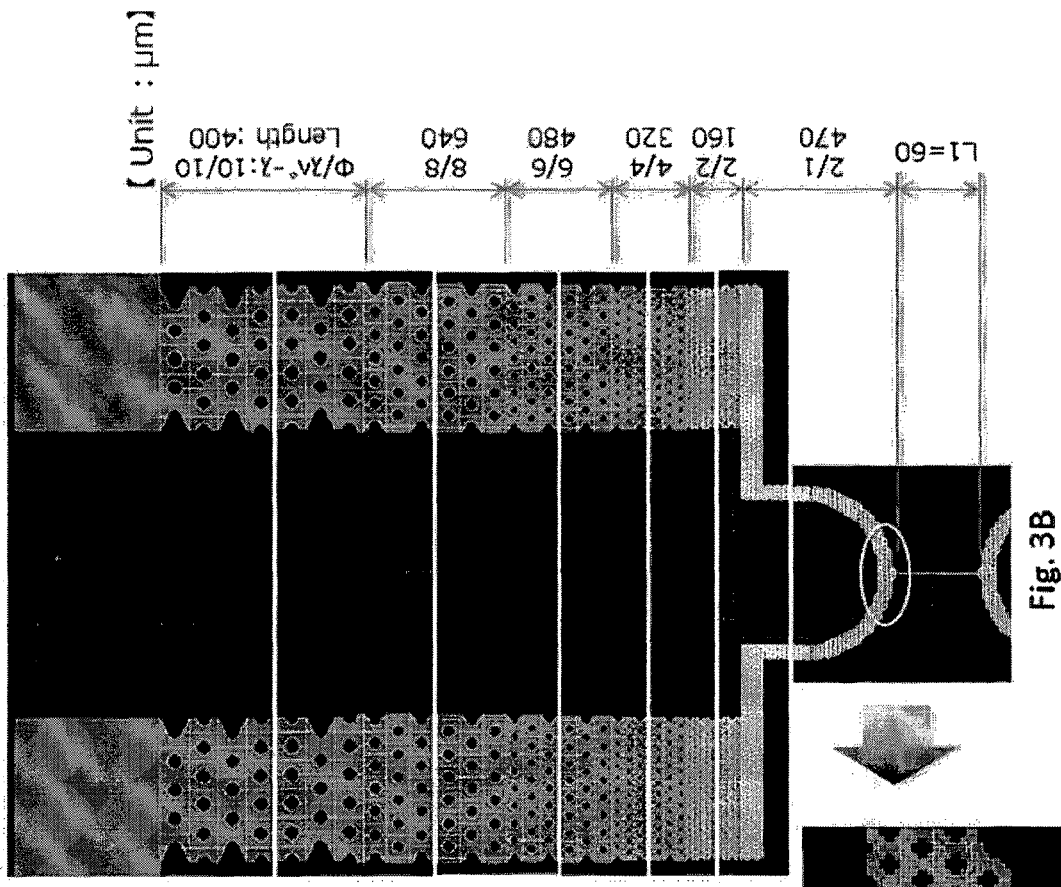
FIGS. 3A-3C illustrate one embodiment of a linearization and filtration system at several levels of magnification.
Figure 3A:
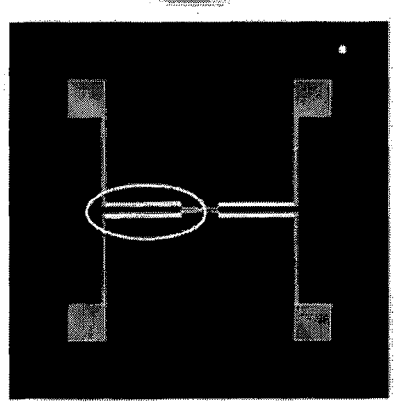
Figure 3B:
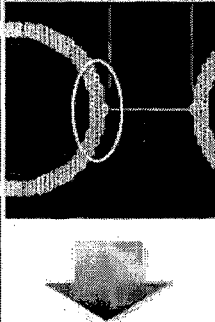
Figure 3C:
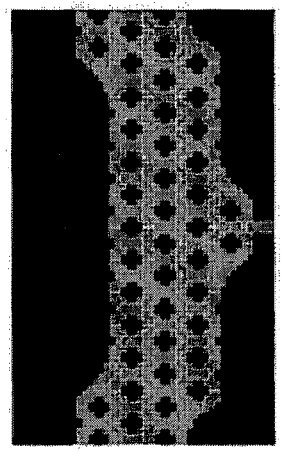

FIG. 3A schematically illustrates a fluidics system with a set of pillars of various sizes positioned in a large channel. FIG. 3B schematically illustrates a higher magnification view of an area around one electrode of the same fluidics system, showing a series of decreasing pillar size and spacing. FIG. 3C schematically illustrates a further close up view of the tip of the electrode of the same fluidics system, wherein pillars are shown as being continued into the space at the tip of the electrode. In these FIGS. 3A-3C), the pillars are shown as filling the large channel, and the pillars are shown as starting with a line of pillar orthogonal to the direction of the fluid flow A spacing between different sizes of the pillars, or different pillars of the same size may have gaps, allowing DNA to be stretched out prior to interacting with a next pillar. In further embodiments, pillars may not be configured to fill a width of a large channel, and may be configured to angle out from a side of a channel to which a nanochannel may be connected. Pillars may further be configured such that pillars may not be aligned such that each line of pillars may be offset from a line of pillars above by half the spacing of a distance between pillars, but may instead be located such that each line is offset by less than one half of a distance between pillars. Pillars may further be arranged such that a width and spacings between pillars may not be uniform across a width of a large channel, but may instead utilize larger spacings and pillar sizes from a side of the large channel opposite nanochannel(s) relative to the side with the nanochannel connected thereto. Pillars may be uniformly locally non-continuous. This configuration may permit larger particles to be excluded from areas of a pillar linearization system, which may have sufficiently small spacings as to catch larger particles, thus preventing clogging of a system. A system may also occasionally have hydrodynamic flow reversed, such that any trapped particles may be flushed out of a system.

Figure 4:
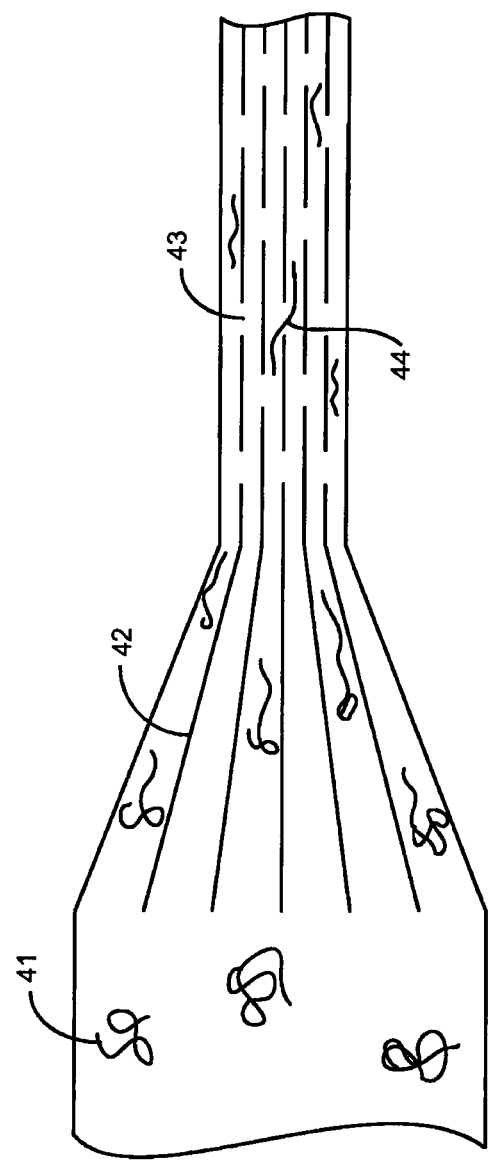
FIG. 4 schematically illustrates a funnel structure which may be utilized to linearize biopolymers.

FIG. 4 schematically illustrates a funnel system for linearizing DNA. Outside of a funnel region DNA may be balled up 41. As DNA flows down funnel section 42 DNA may need to unwind to advance. It may be combined with a parallel channel system that constrains DNA from balling up. In some embodiments a parallel channel system may have gaps 43 that allow DNA migration from one channel to another channel 44. Nanochannels may intersect a channel structure to allow injection of linearized DNA. In some embodiments an electric field and or pressure gradient may be reversed periodically to help with unwinding or unballing of DNA and may allow migration.

In some embodiments much of a DNA sample may flow through a nanochannel without interacting with nanoelectrodes or other sensors. A flow through ananochannel may also be reversed (for example by reversing electrode voltages that control axial motion) to allow an additional opportunity for sequencing of strands that have passed through a nanochannel without interacting with nanoelectrodes or other sensors, or to provide an opportunity to resequence a strand for which data has been obtained.

Figure 6A:
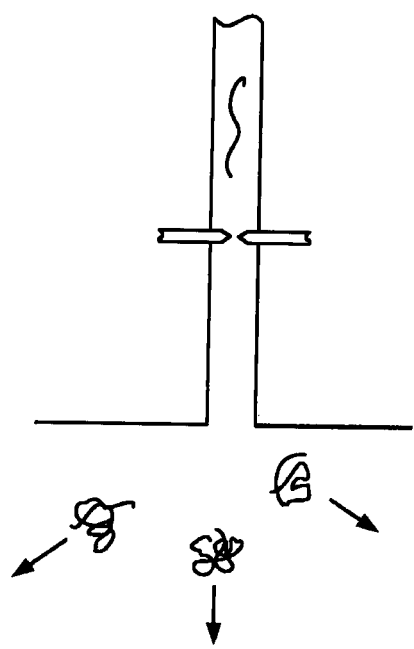
FIGS. 6A-6B schematically illustrates the effects of the drop of electric field strength exiting a nanochannel and the entrapment in that region by a set of nanopillars.

In some embodiments, it may be desirable to send a same biopolymer fragment or group of fragments past a nanoelectrode pair or pairs many times. As shown in FIG. 6A fragments exiting a channel may ball up. Diffusion of molecules may be significant and may in many cases overwhelm electrokinetic or fluid flow velocities. Thus, fragments may re-enter a channel in a different order from which the fragments exited. This may increase the burden on consensus calling software.

Figure 5A:
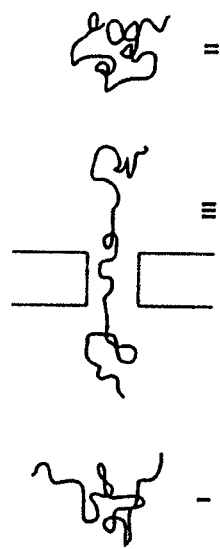
FIGS. 5A-5B schematically illustrate entropic trapping of a biopolymer.
Figure 5B:
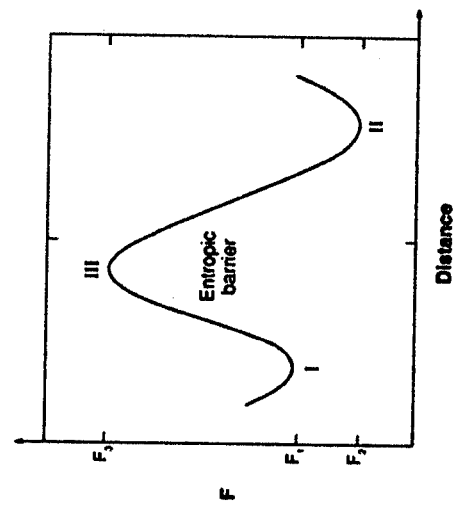

This problem may be ameliorated through entropic trapping. FIG. 5A schematically illustrates a DNA (or other nucleic acid) molecule migrating through a narrow gap. In order to do this it has to unwind, which is a higher energy state. This is shown in FIG. 5B where DNA cannot move from an energy level associated with position Ito an energy level associated with position II without overcoming an energy barrier associated with position III. Thus DNA may not move from position I to position II, unless there is an energy source such as a strong electric field and or pressure gradient.

Figure 6B:
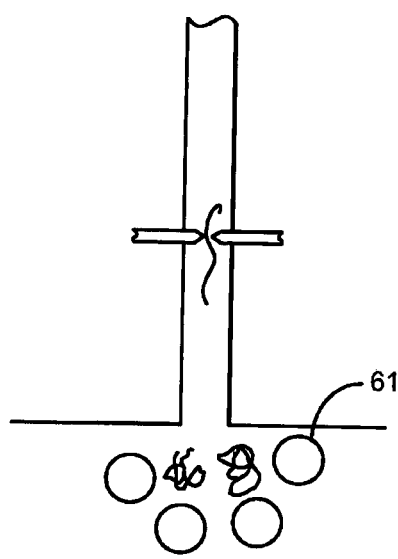

FIG. 6B schematically illustrates one embodiment of an entropic trapping feature (or component) wherein small gaps are created by nanopillars near an exit from a nanochannel. DNA may ball up due to rapid drops in electric field strength after exiting a nanochannel, and may thus have insufficient energy to get through gaps. The DNA may become trapped in a region immediately adjacent an exit of a nanochannel, and may be reinjected for additional measurement opportunities. Because a volume of a region between a nanochannel exit and nanopillars may be small, a same smaller set of biopolymers may be reinjected to allow for simple formation of a consensus sequence for a small set of biopolymers.

Figure 7A:
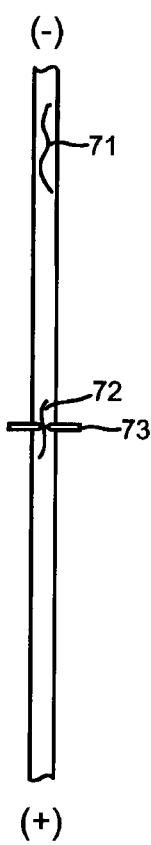
FIGS. 7A-7D schematically illustrates a long channel useful for measuring the same biopolymers multiple times.
Figure 7B:
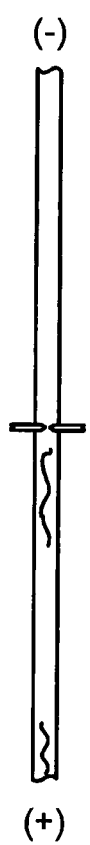
Figure 7C:
Figure 7D:
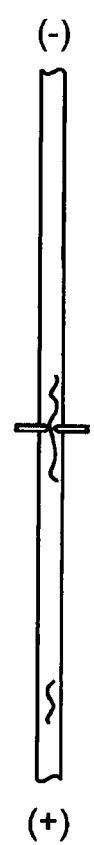

In some embodiments as shown in FIG. 7A-7D, long nanochannels may be utilized to permit resequencing of one or more biopolymers with mixing of the one or more biopolymers with biopolymers in a larger fluidic channel. FIG. 7A-7D show a time course which illustrates how long channels may provide another way to store biopolymers in a manner in which biopolymers may be prevented from mixing with other biopolymers in larger channels, and may further maintain linearization, reducing likelihood of biopolymer entanglement. In some embodiments a channel may be extended on both an inlet and outlet of a nanochannel relative to a nanoelectrode(s) in order to maintain linearization and store biopolymers for remeasurement. FIG. 7A shows a long nanochannel where a short 72 and long 71 DNA fragment are migrating. Because DNA is negatively charged, it may migrate towards a positive electrode. FIG. 7B shows a later time wherein both fragments have migrated past nanoelectrode pairs 73. In FIG. 7C voltage has been reversed and both fragments migrate back past the nanoelectrode pairs. In FIG. 7D voltage has been reversed again allowing a third measurement of these fragments. The process may be repeated as many times as necessary to accurately determine a biopolymer fragment sequence.

In some embodiments, a nanochannel comprises entropic trapping features within the nanochannel, for example at both ends of a nanochannel, whereby a strand of DNA may traverse a length of a nanochannel, and then be unable to leave a nanochannel with the forces being applied to the stand of DNA. The entropic traps may be directional, such that it may be easier to leave an entropic trap in one direction, in comparison with another direction. The entropic traps may be configured such that a direction for which exiting an entropic trapping region may be easier may be in a direction towards a detector region of a nanochannel, and a direction for which exiting an entropic trapping region may be more difficult may be a direction towards an end of a nanochannel, for example where a nananochannel interfaces with a larger channel.

Figure 12:
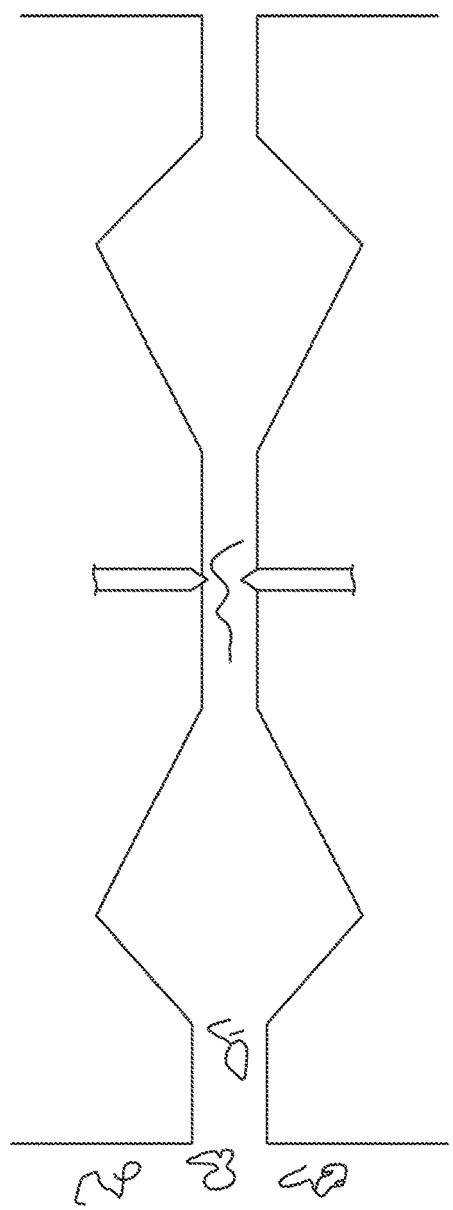
FIG. 12 schematically illustrates a sample nanochannel system for sequencing a biopolymer.

An entropic trapping region may be effectuated by the use of a pillar region as described herein which may be within a nanochannel, or may be effectuated by changes in a cross section of a nanochannel, wherein an entropic trap may comprise a region with a larger cross section, followed by a region with a smaller cross section (FIG. 12).

A direction which may be easier to leave an entropic trapping region may comprise a taper between a larger cross section of a channel, which larger cross section may comprise the entropic trapping region, and a smaller cross section region, while a direction which may be harder to leave an entropic trapping region may comprise an abrupt change in cross section. Different sizes of cross sections, and different amounts and lengths of tapering may allow for greater or lesser ease of leaving an entropic region.

In some examples as shown in FIG. 12, a nanochannel includes an entropic trapping feature that is a region in the nanochannel. The entropic trapping feature may be upstream of a detection region of the nanochannel. The entropic trapping feature may include a first region and a second region. The first region may have an increase in cross-section of the nanochannel and the second region may have a decrease in cross-section of said nanochannel upstream of said detection region. The increase in cross-section in the first region may be abrupt relative to the decrease in cross-section in the second region. An absolute rate of change in cross-section with position in the first region may be greater than an absolute rate of change in cross-section with position in the second region.

The nanochannel may include an additional entropic trapping feature that is a region in the nanochannel. The additional entropic trapping feature may be downstream of the detection region of the nanochannel. The additional entropic trapping feature may include a first region and a second region. The first region may have an increase in cross-section of the nanochannel and the second region may have a decrease in cross-section of said nanochannel downstream of said detection region. The increase in cross-section in the first region may be gradual relative to the decrease in cross-section in the second region. An absolute rate of change in cross-section with position in the first region may be less than an absolute rate of change in cross-section with position in the second region.

A strand of DNA may be made to enter a nanochannel, whereby it may thence be made to pass through a small part of a nanochannel, until reaching an entropic trap, wherein the DNA strand may be being moved with sufficient force to cause the DNA strand to continue to pass through the entropic trapping region without stopping, The DNA strand may then be made to pass through detection regions, where the DNA strand may be detected and may be characterized with respect to one or more parameters, and may then be made to move through much of the length of the nanochannel, until reaching a second entropic trap, wherein the force, which may have been the same level of force which was sufficient to leave the previous entropic trap towards the detection regions of the nanochannel, may be insufficient to leave the second entropic trap towards an end of the nanochannel. The DNA strand may be held in the second entropic trap for a period of time, and thence the field direction may be reversed, causing the DNA strand to reverse direction and move towards and through the detection regions of the nanochannel, and may be made to continue to move until reaching the initial entropic trap, wherein the moving force may be insufficient to cause the DNA strand to leave the initial entropic trap. The DNA strand may thereby be made to move back and forth from one entropic trap to the other and back again for any desired number of movements wherein the DNA strand may be measured and remeasured with each movement through the detection region. A force which may be greater than that used to move the DNA strand back and forth may then be applied, and the DNA strand may thence be made to leave an entropic trap towards an end.

A previously measured DNA strand may be washed away, or made to move a further distance from an end of the nanochannel, and a new strand of DNA may be made to enter the nanochannel, wherein the repeated measuring and remeasuring may be repeated for the new strand of DNA.

Figure 8:
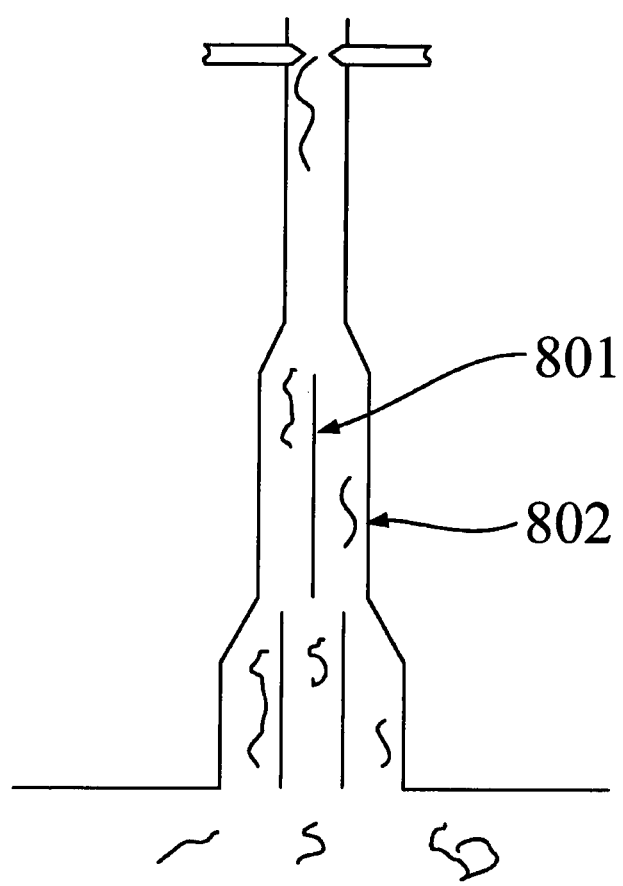
FIG. 8 schematically illustrates a parallel nanochannel device useful for measuring the same biopolymers multiple times.

FIG. 8 schematically illustrates another method to store DNA samples for multiple measurements. A nanochannel may branch periodically into multiple channels. In some embodiments channels may be substantially parallel. In some embodiments a same structure may exist on both sides of nanoelectrode pairs at ends of a nanochannel. Because channels may be narrow, DNA linearization may be maintained. Internal walls 801 may minimize entanglement. As channel cross-section 802 increases, a flow rate of DNA (or other biopolymer) may decrease.

In some embodiments, the device of FIG. 8 may provide more fragment capacity without utilizing the long nanochannel lengths of FIG. 7A-D which may increase a voltage drop across a nanochannel.

After a desired, predetermined or otherwise given number of measurements have been performed utilizing a sample biopolymer(s), sequenced biopolymers may be flushed from a storage channel and replaced with fresh biopolymers. In some embodiments a decision on how much remeasurement is performed may be based on measured data quality and desired confidence levels. Desired accuracy or confidence level may vary between different applications. In some embodiments a quality value may be generated for each sequence, and when an overall quality reaches a desired level of accuracy or confidence level remeasurement may be stopped.

In some embodiments, flushing and replacement of biopolymers may be effectuated by extending time periods for which an electric field may be applied, wherein a same electric field strength as utilized in measuring and remeasuring biopolymer may be utilized. An electric field strength utilized may be increased so as to enable biopolymers to escape from entropy traps. In further embodiments, a pressure and or electric field may be applied to a system so as to move biopolymers, wherein the pressure and or electric field may exert sufficient force as to overcome entropy traps.

Figure 9:
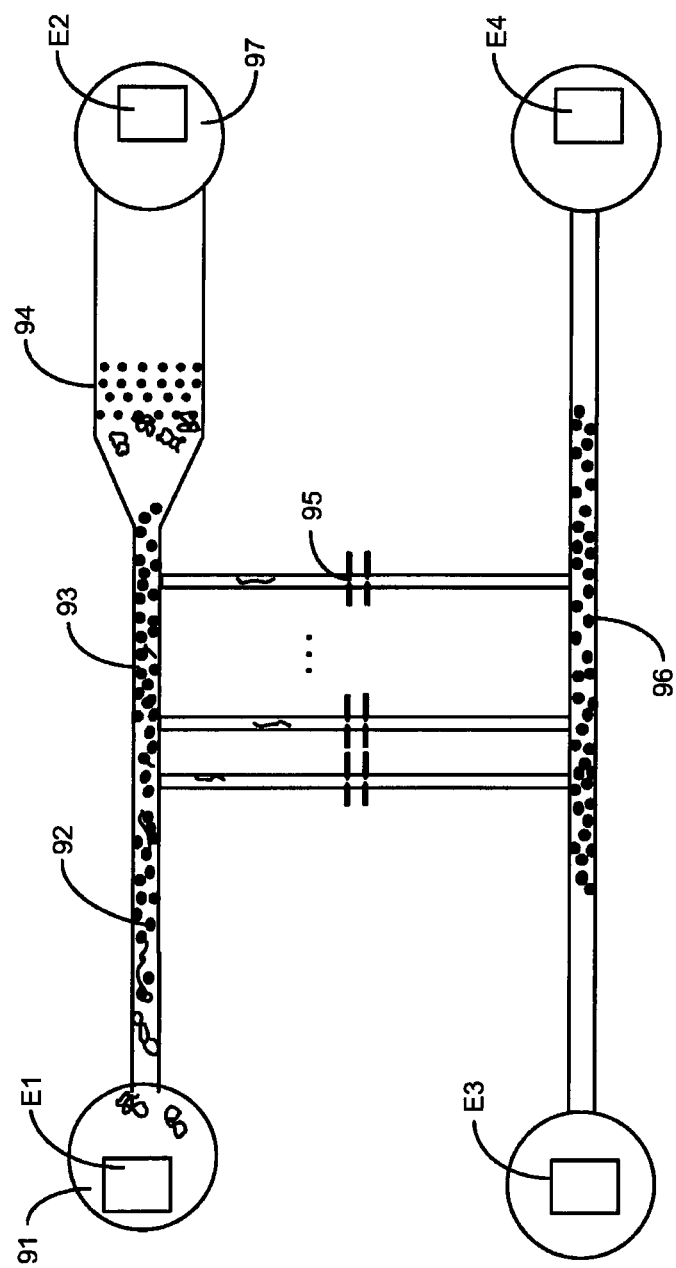
FIG. 9 schematically illustrates a biopolymer capturer and concentrator system.

FIG. 9 schematically illustrates a biopolymer capturer system which combines a set of nanopillars in a larger fluidics channel or entrance fluid channel, which may be used to linearize DNA prior to being directed into a nano branch or nanochannel of a fluidics system. A sample may be introduced utilizing an inlet well 91 and may be moved by electrokinetic and or pressure driven fluid flow to an outlet well 97. Pillars 92 or other gap or pore creating features may cause linearization of DNA or other biopolymers. Gaps or pores 93 between pillars 92 may decrease in size as a biopolymer approaches nanochannels. Electric field strength and or pressure gradient required to linearize DNA may quickly move significant amounts of a sample toward outlet well 97. In some embodiments a field and or pressure may be reversed periodically to keep inlet well 91 or outlet well 97 from being depleted or emptied. Multiple nanochannels may intersect an entrance fluid channel. Multiple nanoelectrode pairs 95 may exist in each nanochannel. One or more electrodes E1 and E2 may be provided in the entrance fluid channel.

In some embodiments, an exit fluid channel may be provided on an outlet end of a nanochannel. One or more electrodes E3 and E4 may be provided in an exit fluid channel. In some embodiments wells associated with an exit channel may be flushed by a combination of fluidic flow and or electrokinetic flow. Nanopillars 96 may exist in an exit fluid channel to minimize diffusion of DNA exiting the nanochannels, or to linearize DNA for reinjection.

In some embodiments a biopolymer concentration of a provided biopolymer sample may not be optimal. If a concentration is too low there may be large regions of data wherein no biopolymers may be measured between regions of data wherein biopolymer fragments may be measured. In some embodiments a sample may be tested, which may utilize nanoelectrodes 95 in nanochannel(s), and if a biopolymer concentration is too high additional fluid may be added to the sample.

In some cases, a provided biopolymer sample may have too low of a concentration of biopolymers. In some embodiments entropic trapping may be used to concentrate the sample. FIG. 9 shows one embodiment of a sample concentrator. In a section beyond nanochannels an entrance fluid channel increases in width with no obstructions. Further downstream is a biopolymer dam area 94 with small gaps. Such gaps may be due to nanopillars, porous silicon or other gap narrowing approaches. A biopolymer may ball up and not move through biopolymer dam area 94. Because a cross section of an entrance fluid channel may be wide here, an electric field and or fluid flow rate may not be high enough to linearize a biopolymer so that the biopolymer may fit through gaps in biopolymer dam region 94 so as to cause entropic trapping. After concentration an electric field or fluid flow direction may be reversed to allow a biopolymer to migrate back with respect to the nanochannels for injection or reinjection into the nanochannels.

In some cases, a provided biopolymer sample may have mixtures of different biopolymer lengths wherein only certain fragment sizes are of interest. In some embodiments entropic trapping may be used to purify a desired biopolymer size from other sizes. In sequencing of DNA or other biopolymers, longer fragments make assembly more efficient. For example if only long biopolymer fragments are of interest the biopolymer dam area 94 may be used to only trap longer biopolymer fragments. An electric field or fluid flow rate may be increased to provide enough energy for small molecules to escape an entropic trap. Larger biopolymers may then be injected by reversing an electric field or fluid flow direction to allow injection of the larger biopolymers captured by biopolymer dam area 94.

In some applications, it may be desirable to sequence smaller biopolymers. Entropic trapping may be used to purify out smaller biopolymer fragments from larger biopolymer fragments, wherein larger fragments may be trapped by an entropic trap, while desired smaller fragments may be permitted to pass. In some embodiments multiple entropic traps can be used, for example wherein a first entropic trap may be utilized to retain undesired larger biopolymers or biopolymer fragments, while a second entropic trap may be utilized to capture desired smaller biopolymer fragments or biopolymers; desired smaller biopolymers or biopolymer fragments may then be fluidically or electrokinetically manipulated for detection or for use in a bioassay. Both local pore size and or local channel cross section may be varied along with electric field and or fluid flow rate to capture or pass different sizes of biopolymers. Electric field or fluid flow rate may be controlled by software so as to allow entropic trapping approach to provide a software controllable size filter.

Figure 10:
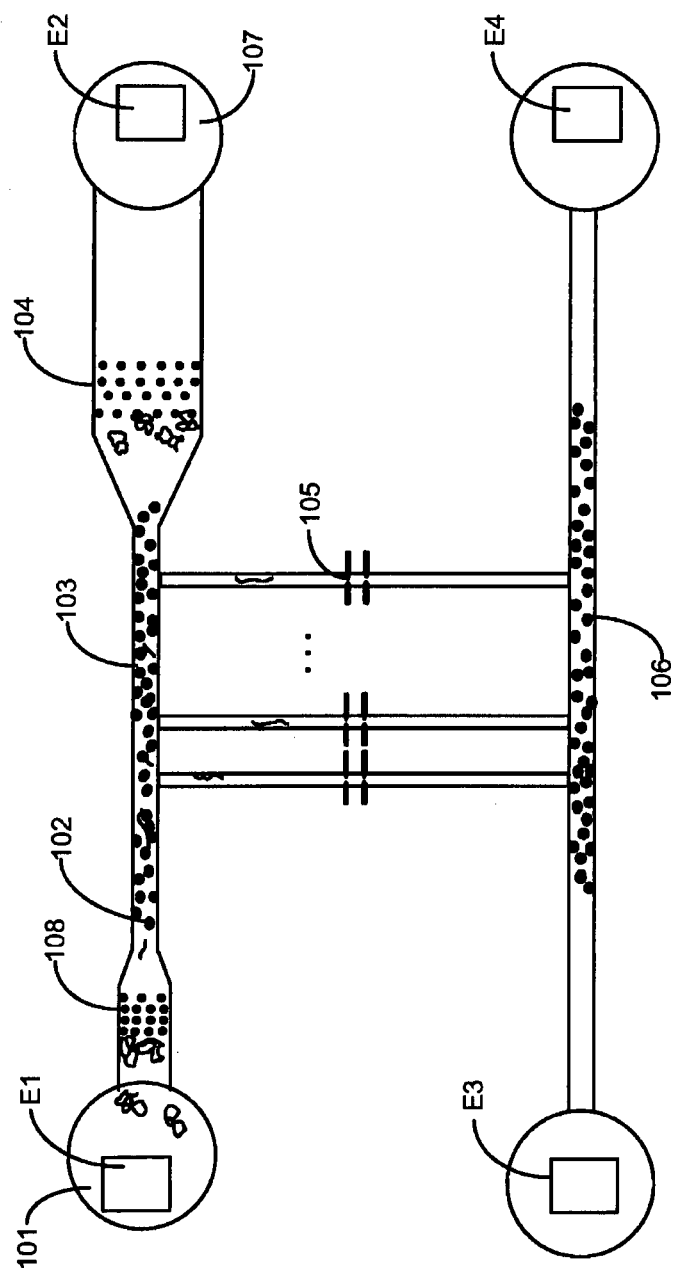
FIG. 10 schematically illustrates a biopolymer capturer, purifier, and concentrator system.

In some embodiments, entropic traps may be used to both purify and concentrate biopolymers. FIG. 10 schematically illustrates a biopolymer capturer system which combines purification and concentration. A sample biopolymer may be introduced utilizing an inlet well 101, and may be moved by electrokinetic and or pressure driven fluid flow to an outlet well 107. The biopolymer may interact with a first biopolymer dam 108. This dam may have a moderate level of entropic trapping so large biopolymers may be trapped while smaller biopolymers or other moieties which are not desired may pass through, providing a form of purification. A set of nanopillars may be utilized in a larger fluidics channel or entrance fluid channel, which may be used to linearize DNA prior to being directed into a nano branch or nanochannel of the fluidics system. Pillars 102 or other gap or pore creating features may cause linearization of the DNA or other biopolymer. The gaps or pores 103 between pillars 102 may decrease in size as a biopolymer approaches nanochannels. A field and or pressure gradient required to linearize DNA may quickly move significant amounts of a sample toward outlet well 107. In some embodiments a field and or pressure may be reversed periodically to keep inlet well 101 or outlet well 107 from being depleted or emptied. Multiple nanochannels may intersect an entrance fluid channel. Multiple nanoelectrode pairs 105 may exist in different nanochannels. One or more electrodes E1 and E2 may be provided in an entrance fluid channel. In some embodiments, a second biopolymer dam area 104 with a higher level of entropic trapping may be utilized. Smaller fragments that may move through first biopolymer dam 108 may be trapped by second biopolymer dam area 104, enabling concentration. Once concentrated, DNA may be moved backwards for injection into a nanochannel.

Computer Systems

Figure 11:
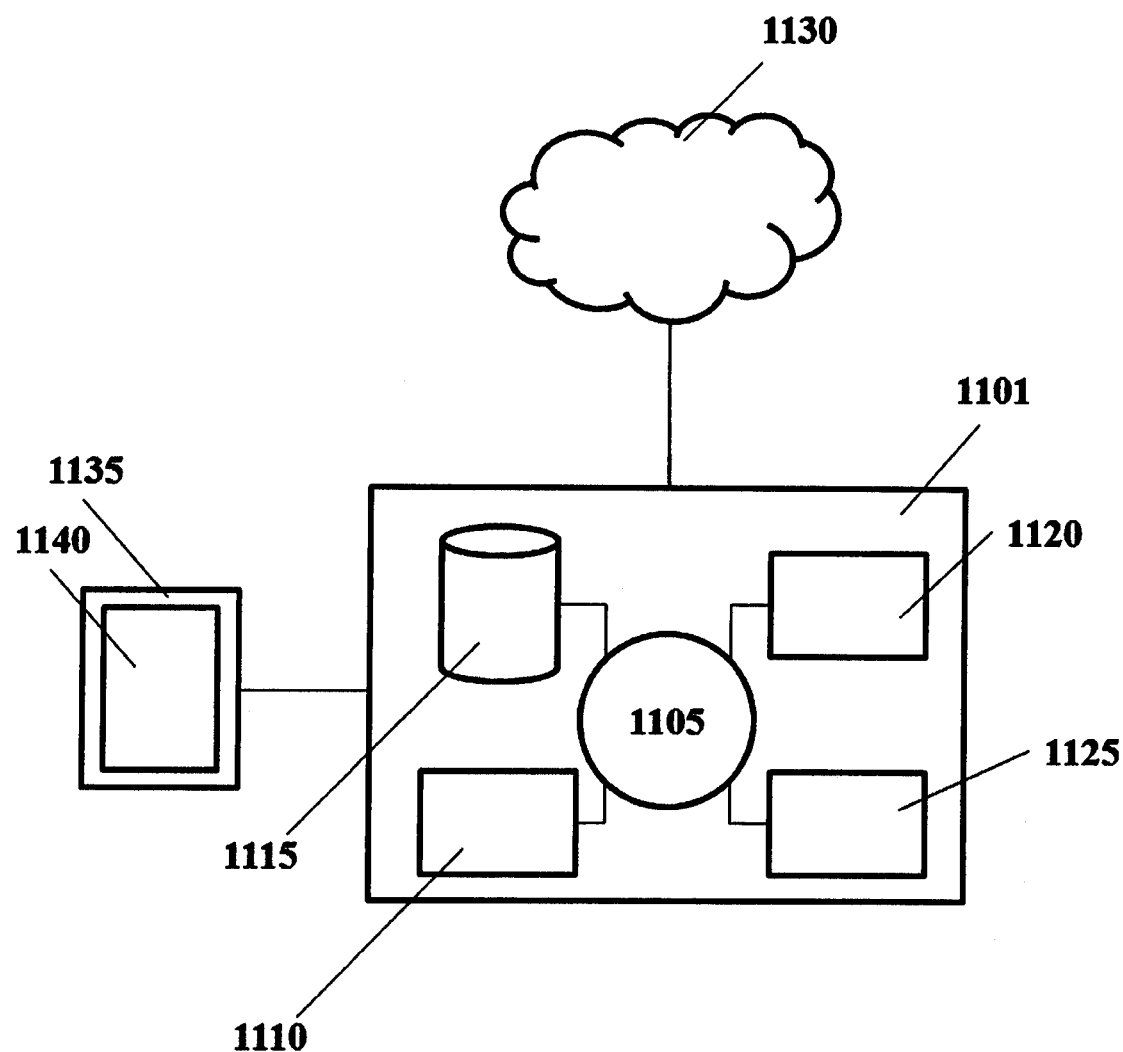
FIG. 11 schematically illustrates a computer system that is programmed or otherwise configured to implement devices, systems and methods of the present disclosure.

The present disclosure provides computer control systems that are programmed or otherwise configured to implement methods provided herein, such as calibrating sensors of the present disclosure. FIG. 11 shows a computer system 1101 that includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet. The computer system 1101 can communicate with one or more remote computer systems through the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine having a processer adapted to execute the code, or can be compiled during runtime. The code can be supplied in a programming language that can be selected to enable the code to execute in a pre-compiled or as-compiled fashion.

The computer system 1101 can be programmed or otherwise configured to regulate one or more processing parameters, such as the substrate temperature, precursor flow rates, growth rate, carrier gas flow rate and reaction chamber pressure. The computer system 1101 can be in communication with valves between the storage vessels and a reaction chamber, which can aid in terminating (or regulating) the flow of a precursor to the reaction chamber.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Methods and systems of the present disclosure can be implemented by way of one or more algorithms. An algorithm can be implemented by way of software upon execution by the central processing unit 1105.

Devices, systems and methods of the present disclosure may be combined with and/or modified by other devices, systems, or methods, such as those described in, for example, JP 2013-36865A, US 2010/0025249, US 2012/0193237, US 2012/0322055, US 2013/0001082, US 2014/0300339, JP 2011-163934A, JP 2005-257687A, JP 2011-

163934A and JP 2008-32529A, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby. All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

The invention claimed is:

1. A system for sequencing a biopolymer, comprising:
   a nanochannel having a detection region for detecting said biopolymer or a portion thereof upon flow of said biopolymer through said detection region; and
   a first entropic trapping component and a second entropic trapping component disposed in or adjacent to said nanochannel, wherein (i) said first entropic trapping component is operable to linearize said biopolymer upon flow of said biopolymer through said first entropic trapping component and towards a first side of said detection region, and (ii) said second entropic trapping component is operable to linearize said biopolymer upon flow of said biopolymer through said second entropic trapping component and towards a second side of said detection region, which first side is different from said second side,
   wherein said first entropic trapping component is in said nanochannel, and wherein said first entropic trapping component includes an increase in cross-section of said nanochannel followed by a decrease in cross-section of said nanochannel towards said detection region.

2. The system of claim 1, wherein said first and/or second entropic trapping component permits movement of said biopolymer back and forth in said nanochannel.

3. The system of claim 1, further comprising a fluid channel adjacent to an end of said nanochannel, which fluid channel is larger in cross-section than said nanochannel.

4. The system of claim 3, wherein said fluid channel is at least five times larger in cross-section than said nanochannel.

5. The system of claim 4, wherein said fluid channel is at least ten times larger in cross-section than said nanochannel.

6. The system of claim 3, wherein said fluid channel and said nanochannel are integrated in a substrate.

7. The system of claim 3, further comprising an additional fluid channel adjacent to an additional end of said nanochannel, wherein said additional fluid channel is larger in cross-section than said nanochannel.

8. The system of claim 3, wherein said fluid channel is arranged to permit a fluid containing said biopolymer to flow around said detection region.

9. The system of claim 1, wherein said first and/or second entropic trapping component is configured to entropically trap and concentrate said biopolymer.

10. The system of claim 1, wherein said detection region comprises a pair of electrodes that are spaced apart by a gap, and wherein said pair of electrodes is operable to detect an electrical current across said gap upon flow of said biopolymer through said gap.

11. The system of claim 10, wherein said pair of electrodes comprises tunneling electrodes.

12. The system of claim 11, wherein said electrical current comprises a tunneling current.

13. The system of claim 11, wherein said gap has a spacing that is adjustable.

14. The system of claim 1, wherein said first and/or second entropic trapping component permits flow of said biopolymer towards said detection region at a greater flow rate than away from said detection region.

15. The system of claim 1, wherein said second entropic trapping component includes an increase in cross-section of said nanochannel followed by a decrease in cross-section of said nanochannel away from said detection region.

16. The system of claim 15, wherein in said second entropic trapping component, said decrease in cross-section is abrupt relative to said increase in cross-section.

17. The system of claim 1, wherein in said first entropic trapping component, said increase in cross-section is abrupt relative to said decrease in cross-section.

18. The system of claim 1, wherein said first entropic trapping component is upstream of said detection region and said second entropic trapping component is downstream of said detection region, or vice versa.

\* \* \* \* \*